(12) United States Patent
Clarke et al.

(10) Patent No.: US 10,568,933 B2
(45) Date of Patent: Feb. 25, 2020

(54) BETA-CASEIN A2 AND BLOOD GLUCOSE LEVELS

(71) Applicant: THE A2 MILK COMPANY LIMITED, Auckland (NZ)

(72) Inventors: Andrew John Clarke, Auckland (NZ); Malav Suchin Trivedi, Hollywood, FL (US)

(73) Assignee: THE A2 MILK COMPANY LIMITED, Auckland (NZ)

( * ) Notice: Subject to any disclaimer, the term of this patent is extended or adjusted under 35 U.S.C. 154(b) by 0 days.

(21) Appl. No.: 14/913,525

(22) PCT Filed: Aug. 22, 2014

(86) PCT No.: PCT/NZ2014/000172
§ 371 (c)(1),
(2) Date: Feb. 22, 2016

(87) PCT Pub. No.: WO2015/026245
PCT Pub. Date: Feb. 26, 2015

(65) Prior Publication Data
US 2016/0324922 A1 Nov. 10, 2016

Related U.S. Application Data

(60) Provisional application No. 61/869,213, filed on Aug. 23, 2013.

(51) Int. Cl.
*A23L 33/19* (2016.01)
*A23L 33/00* (2016.01)
*A61K 38/17* (2006.01)
*A23K 20/147* (2016.01)

(52) U.S. Cl.
CPC ........ *A61K 38/1709* (2013.01); *A23K 20/147* (2016.05); *A23L 33/19* (2016.08); *A23L 33/30* (2016.08); *A23L 33/40* (2016.08); *A23V 2002/00* (2013.01)

(58) Field of Classification Search
CPC ....... A23K 20/147; A23L 33/19; A23L 33/30; A23L 33/40; A23V 2002/00; A61K 38/1709
See application file for complete search history.

(56) References Cited

U.S. PATENT DOCUMENTS

2003/0221200 A1 11/2003 McLachlan
2006/0280802 A1* 12/2006 Campbell .......... A61K 38/1709
424/535

FOREIGN PATENT DOCUMENTS

| EP | 2745709 A1 | 6/2014 | |
|---|---|---|---|
| WO | WO-1996/014577 A1 | 5/1996 | |
| WO | WO-1996/036239 A1 | 11/1996 | |
| WO | WO 0100047 A1 * | 1/2001 | ............. A23C 9/152 |
| WO | WO-2001000047 A1 | 1/2001 | |
| WO | WO-2002/019832 | 3/2002 | |
| WO | WO-2004/030690 A1 | 4/2004 | |
| WO | WO 2004030690 A1 * | 4/2004 | ......... A61K 38/1709 |

OTHER PUBLICATIONS

Ginsberg, Diabetes and dyslipidemia, Heart Fail Monit. 2001;2(1):1420.*
World Health Organization, WHO, Diabetes programme, ABout diabetes, published online 2006.*
McGarrigle, BANT Featured Article, published online Jul. 3, 2013.*
Diapedia, Hyperglycaemia without diabetes—Associated disorders—Diapedia, The Living Textbook of Diabetes , accessed on Mar. 18, 2018.*
James B. Meigs, Fasting Plasma Homocysteine Levels in the Insulin Resistance Syndrome , Diabetes Care 24:1403-1410, 2001.*
Bell et al, Health Implications of Milk Containing β-Casein with the A2 Genetic Variant, *Critical Reviews in Food Science and Nutrition*, (46): 93-100 (2006).
Elliott et al., Type I (insulin dependent) diabetes mellitus and cow milk: casein variant consumption, *Diabetologia*, (42): 292-6 (1999).
Kaminski et al., Polymorphism of bovine beta-casein and its potential effect on human health, *J Appl Genet*, 3 (48): 189-198 (2007).
Trivedi et al., Morphine Induces Redox-Based Changes in Global DNA Methylation and Retrotranscription by Inhibition of Excitatory Amino Acid Transporter Type 3-Mediated Cystine Uptake, Mol. Pharm., 85:747-57 (2014).
International Search Report and Written Opinion of the International Search Authority, Australian Patent Office, PCT/NZ2014/000172 dated Aug. 23, 2013.
International Preliminary Report on Patentability, Australian Patent Office, PCT/NZ2014/000172 dated Aug. 23, 2013.

* cited by examiner

*Primary Examiner* — Rachael E Bredefeld
*Assistant Examiner* — Erinne R Dabkowski
(74) *Attorney, Agent, or Firm* — Marshall, Gerstein & Borun LLP

(57) ABSTRACT

Regulating the level of glucose in the blood of an animal comprising the consumption by the animal of a composition containing beta-casein, or providing the composition to the animal for consumption, where the beta-casein comprises at least 75% by weight beta-casein A2. Uses include managing the symptoms of hyperglycaemia and associated conditions including diabetes. The effect is both acute (post-exposure to the composition) and ongoing.

8 Claims, 6 Drawing Sheets
Specification includes a Sequence Listing.

BETA-CASEIN A2 AND BLOOD GLUCOSE LEVELS

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 47954A_Seqlisting.txt; Size: 1,327 bytes, created: May 24, 2016.

TECHNICAL FIELD

The invention relates to the milk protein beta-casein A2 and regulating the levels of glucose in blood. In particular, the invention relates to milk and milk derived food products. The applicant has found that the consumption of milk and milk products that contain high levels of the protein beta-casein A2 and the avoidance of milk and milk products containing beta-casein A1 helps regulate or maintain glucose levels in blood. Regulation of blood glucose levels is beneficial for the management of a number of health problems associated with hyperglycaemia, including the symptoms of type I and type II diabetes. Notably, the beneficial effect is immediate (acute) and additionally induces an ongoing (post-exposure to beta-casein A1) beneficial predisposition to regulating or maintaining blood glucose levels.

BACKGROUND OF THE INVENTION

Blood glucose levels, often referred to as blood sugar levels or concentrations, refer to the amount of glucose present in the blood of a human or animal. Blood glucose levels fluctuate throughout the day, being lowest in the morning before eating, rising for an hour or two following each meal. The primary function of glucose is a source of energy. Glucose from the diet enters the bloodstream from the intestines and is made available for cell absorption via insulin. Glucose may also be produced endogenously from carbohydrates or amino acid R-group side chain substrates through gluconeogenesis when sufficient dietary glucose is available.

The levels of glucose in the blood are tightly regulated in mammals by metabolic processes. The human body maintains glucose levels at close to constant levels most of the day. Insulin signaling directs the body's cells to take up glucose for their own use. If the glucose level inside cells is high, some glucose will be converted to the insoluble glycogen to prevent the soluble glucose from interfering with cellular metabolism. This lowers blood glucose levels and helps prevent hyperglycemia. A deficiency in insulin or the compromised ability to respond to insulin leads to diabetes. Glycogen is held as an energy reserve in the liver and in muscle tissue. If a person's glycogen stores are full, extra glucose will be converted to fat and stored.

Hyperglycemia refers to a state of persistently high levels of blood glucose. Diabetes mellitus is the most prominent disease resulting from a failure of blood sugar regulation. The classical symptoms of high blood sugar include frequent urination (polyuria), increased thirst (polydipsia) and increased hunger (polyphagia). Long term complications directly linked to hyperglycemia include cardiovascular disease, chronic renal failure, and diabetic retinopathy.

Type I diabetes results from the body's failure to produce insulin, and is sometimes referred to as insulin-dependent diabetes or juvenile diabetes. Those suffering from type I diabetes typically control insulin levels, and consequently blood glucose levels, by injecting insulin. Type II diabetes stems from resistance to insulin, where cells fail to use or respond to insulin properly, and is sometimes referred to as adult-onset diabetes. Both type I and type II diabetes are chronic conditions that cannot be cured. Medical intervention therefore targets prevention of hyperglycemia and also management of the symptoms once hyperglycemia has been diagnosed.

Milk, mainly bovine milk, consumed in populations throughout the world, is a major source of protein in human diets. Bovine milk typically comprises around 30 grams per litre of protein. Caseins make up the largest component (80%) of that protein, and beta-caseins make up about 37% of the caseins. In the past two decades the body of evidence implicating casein proteins, especially beta-caseins, in a number of health disorders has been growing.

The beta-caseins can be categorised as beta-casein A1 and beta-casein A2. These two proteins are the predominant beta-caseins in milk consumed in most human populations. Beta-casein A1 differs from beta-casein A2 by a single amino acid. A histidine amino acid is located at position 67 of the 209 amino acid sequence of beta-casein A1, whereas a proline is located at the same position of beta-casein A2. This single amino acid difference is, however, critically important to the enzymatic digestion of beta-caseins in the gut. The presence of histidine at position 67 allows a protein fragment comprising seven amino acids, known as beta-casomorphin-7 (BCM-7), to be produced on enzymatic digestion. Thus, BCM-7 is a digestion product of beta-casein A1. In the case of beta-casein A2, position 67 is occupied by a proline which hinders cleavage of the amino acid bond at that location. Thus, BCM-7 is not a digestion product of beta-casein A2.

Other beta-casein variants, such as beta-casein B and beta-casein C, also have histidine at position 67, and other variants, such as A3, D and E, have proline at position 67. But these variants are found only in very low levels, or not found at all, in milk from cows of European origin. Thus, in the context of this invention, the term beta-casein A1 refers to any beta-casein having histidine at position 67, and the term beta-casein A2 refers to any beta-casein having proline at position 67.

BCM-7 is an opioid peptide and can potently activate opioid receptors throughout the body. BCM-7 has the ability to cross the gastrointestinal wall and enter circulation enabling it to influence systemic and cellular activities via opioid receptors. The applicant and others have previously determined a link between the consumption of beta-casein A1 in milk and milk products and the incidence of certain health conditions including type I diabetes (WO 1996/014577), coronary heart disease (WO 1996/036239) and neurological disorders (WO 2002/019832). WO 1996/014577 describes the triggering of type I diabetes in humans by the ingestion of milk and milk products that contain beta-casein A1. It is considered that beta-casein A1 stimulates diabetogenic activity, i.e. may cause humans to become diabetic.

The applicant has now found conclusive scientific evidence for a direct link between the consumption of beta-casein A1 and blood glucose levels, and also the consumption of beta-casein A1 and the development of insulin resistance. Since elevated blood glucose levels are implicated in a number of adverse health conditions, including types I and II diabetes, and weight management conditions such as metabolic syndrome (syndrome X) and obesity, the applicant has found a new way to treat these conditions or manage the symptoms of these conditions. Importantly, the applicant has found evidence, not only of an acute and undesirable response to the consumption of beta-casein A1, but also of an ongoing (post-exposure to beta-casein A1 or BCM-7) response in that the consumption of beta-casein A1, and resultant production of BCM-7, can induce genetic changes in an animal that lead to higher levels of blood glucose and consequently an increased likelihood of causing symptoms associated with high blood glucose levels.

It is therefore an object of the invention to provide a method for controlling the levels of glucose in blood, or to at least provide a useful alternative to existing methods.

SUMMARY OF THE INVENTION

In a first aspect of the invention there is provided the use of a composition for regulating the level of glucose in the blood of an animal, where the composition contains beta-casein, and where the beta-casein comprises at least 75% by weight beta-casein A2.

In a second aspect of the invention there is provided a composition for regulating the level of glucose in the blood of an animal which composition contains beta-casein and where the beta-casein comprises at least 75% by weight beta-casein A2.

In another aspect of the invention there is provided the use of milk in the manufacture of a composition for regulating the level of glucose in the blood of an animal where the milk contains beta-casein and where the beta-casein comprises at least 75% by weight beta-casein A2.

In another aspect there is provided the use of beta-casein A2 in the manufacture of a composition for regulating the level of glucose in the blood of an animal where the composition comprises at least 75% by weight beta-casein A2. The beta-casein A2 is preferably a component of milk. The milk is preferably bovine milk.

In a further aspect of the invention there is provided a method for regulating the level of glucose in the blood of an animal comprising the consumption by the animal of a composition containing beta-casein, or providing the composition to the animal for consumption, where the beta-casein comprises at least 75% by weight beta-casein A2. The amount of beta-casein A2 may be any amount in the range of 75% to 100% by weight of the beta-casein, for example at least 90% or even 100%.

In certain embodiments of the invention, the composition is milk or a milk product. The milk may be milk powder or liquid milk. The milk product may be cream, yoghurt, quark, cheese, butter, ice cream, or any other milk product.

The level of glucose in the blood may be regulated for one or more purposes including avoiding or reducing the symptoms of diabetes, preventing conditions associated with diabetes including cardiovascular disease, chronic renal failure, and diabetic retinopathy, and the management of weight particularly for preventing or treating obesity.

The response to consumption of the composition by the animal may be an acute response and may additionally induce a predisposition in the animal to an elevated level of glucose in the blood of the animal.

In most embodiments of the invention, the animal is a human. However, in other embodiments, the animal may be a dog, cat, or any other domestic animal where feed is supplemented with milk.

DETAILED DESCRIPTION

Figure 1:
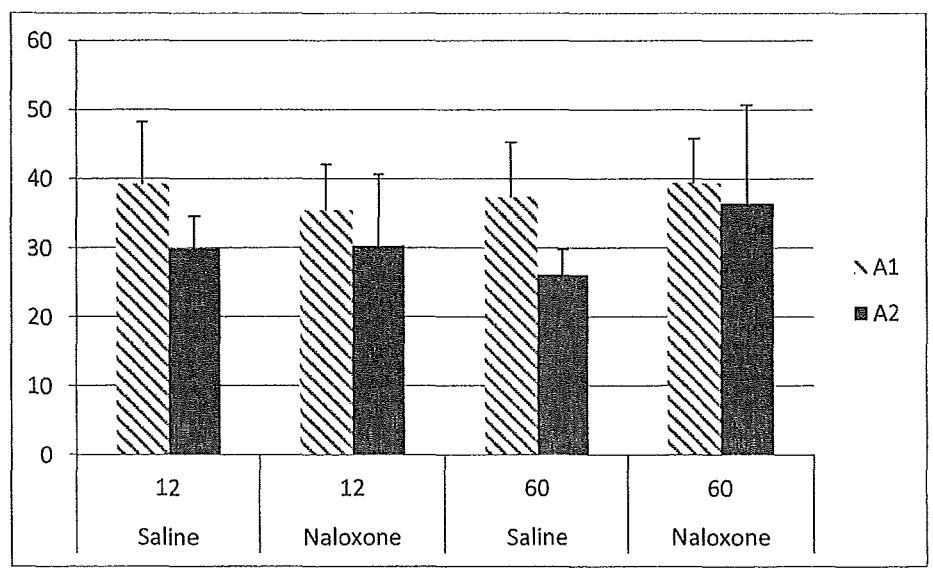
FIG. 1 shows jejunum DPPIV activity on acute and chronic feeding of rats fed the diets of Example 1.

The invention relates to a composition containing the protein beta-casein and its use for regulating blood glucose levels in animals, especially humans. Importantly, the beta-casein is the A2 variant of beta-casein. The beta-casein in the composition is 100% beta-casein A2, or makes up at least 75% by weight of the total beta-casein variants present in the composition. The importance of the predominance of the A2 variant in the composition is due to the fact that the applicant has shown that there is a direct link between the A1 variant and high levels of DPPIV activity in the jejunum in animals. High levels of DPPIV activity are directly associated with high blood glucose levels. An inference of high levels of glucose in the blood of humans on consumption of beta-casein A1 therefore has scientific basis. The applicant has also found that consumption of milk containing only beta-casein A2 or predominantly beta-casein A2 results in elevated levels of insulin receptor and insulin receptor substrate gene expression. This improves the ability to manage glucose homeostasis, reduces symptoms and complications associated with elevated blood glucose levels, and lowers the risk of type II diabetes developing.

The term "acute" as used in this specification, unless otherwise indicated, is intended to mean during the period of time from consumption of beta-casein A1 to exit of beta-casein A1 or BCM-7 from the gut (typically 8-20 hours after consumption).

Since the primary, if not only, source of beta-caseins in the diet of most human populations is milk or products derived from milk, and since most milk consumed contains a mixture of the A1 and A2 variants of beta-casein only, the consumption of milk (or products made from such milk) having a high content of the A2 variant will necessarily mean that the consumption of the A1 variant is low. It can then be understood that if the only dietary source of beta-casein contains the A2 variant and no other variant, the dietary intake of the A1 variant is eliminated and the adverse symptoms of high blood glucose levels can therefore also be expected to be eliminated.

Accordingly, the invention of this application is based on the reduction or elimination of beta-casein A1 in the diet, and the promotion of beta-casein A2, and this is achieved by ensuring that the beta-casein in beta-casein containing food compositions, especially milk and milk products, is predominantly or even exclusively beta-casein A2.

Ideally, the beta-casein in the composition is 100% beta-casein A2. The complete elimination of beta-casein A1 therefore maximises the potential to maintain normal levels of blood glucose and therefore the avoidance of adverse symptoms associated with high levels, particularly in the case of diabetics. However, the symptoms may be reduced in any composition where the beta-casein is predominantly beta-casein A2, for example, any amount between 75% by weight and 100%, including but not limited to 80%, 90%, 95%, 98% and 99% by weight.

The composition of the invention is typically milk, but may also be any milk-derived product such as cream, yoghurt, quark, cheese, butter, or ice cream. The composition may also be a non-milk product containing beta-casein that has been obtained from milk. The composition may be beta-casein itself, or may be prepared from beta-casein, which beta-casein may be in solid form such as powder or granules or in the form of a solid cake.

While the milk may be obtained from any mammal, including humans, goats, pigs and buffalo, in preferred embodiments of the invention the milk is bovine milk.

The milk may be in the form of fresh milk, milk powder, liquid milk reconstituted from a powder, skim milk, homogenised milk, condensed milk, evaporated milk, pasteurised milk or non-pasteurised milk, or any other form of milk.

The composition of the invention is applicable for consumption by humans primarily, but it should be appreciated that the health benefit is also relevant for some other animals such as cats, dogs and other domestic animals.

Support for the invention is found in the experiments described in the Examples.

Example 1 sets out the feeding methodology for the rat studies of Example 2. The diets are shown in Table 1. The A1 milk diet is based on a formulation where all the beta-casein in the diet is beta-casein A1. The A2 milk diet is based on a formulation where all the beta-casein in the diet is beta-casein A2. The control diet is based on a formulation where the protein content is egg white.

Example 2 relates to the effect of beta-casein A1 and beta-casein A2 diets on dipeptidyl peptidase IV (DPPIV) activity in the jejunum and colon of rats. DPPIV is a protease known to play an important part of glucose metabolism. DPPIV inactivates incretins, which are hormones that cause an increase in secreted insulin and a corresponding decrease in glucagon, and also slow the rate of absorption of nutrients (including glucose and its precursor polysaccharides) into the blood stream by reducing gastric emptying. The main incretins are glucagon-like peptide-1 (GLP-1) and gastric inhibitory peptide (GIP). An increase in DPPIV activity means that the levels of incretins will be lowered. Since incretins cause insulin to be released, the levels of insulin will be reduced and consequently blood glucose levels will increase. In addtion, lower levels of incretins leads to increased gastric emptying and therefore to increased blood glucose levels. In other words, a lowering of DPPIV activity should lead to lower blood glucose levels.

Figure 2:
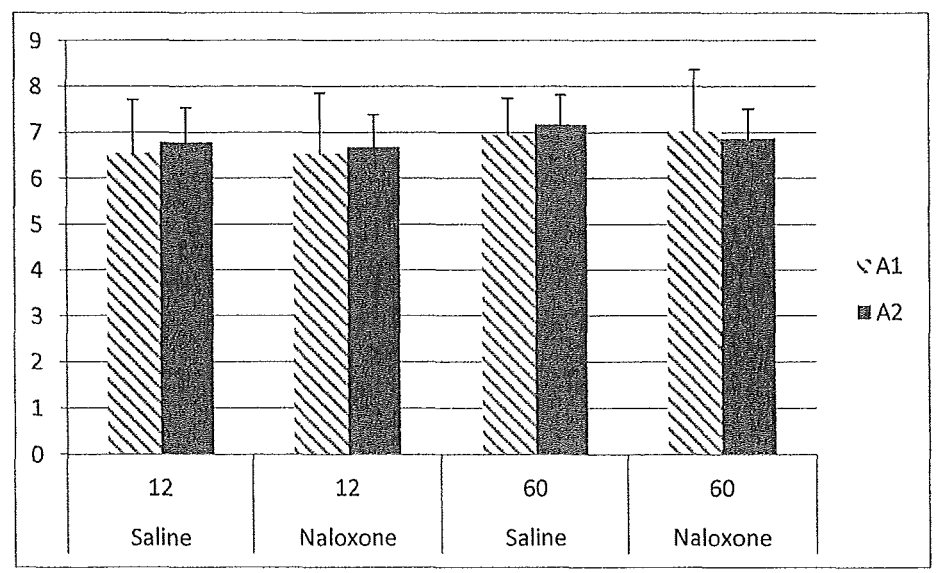
FIG. 2 shows colon DPPIV activity on acute and chronic feeding of rats fed the diets of Example 1.
Figure 3:
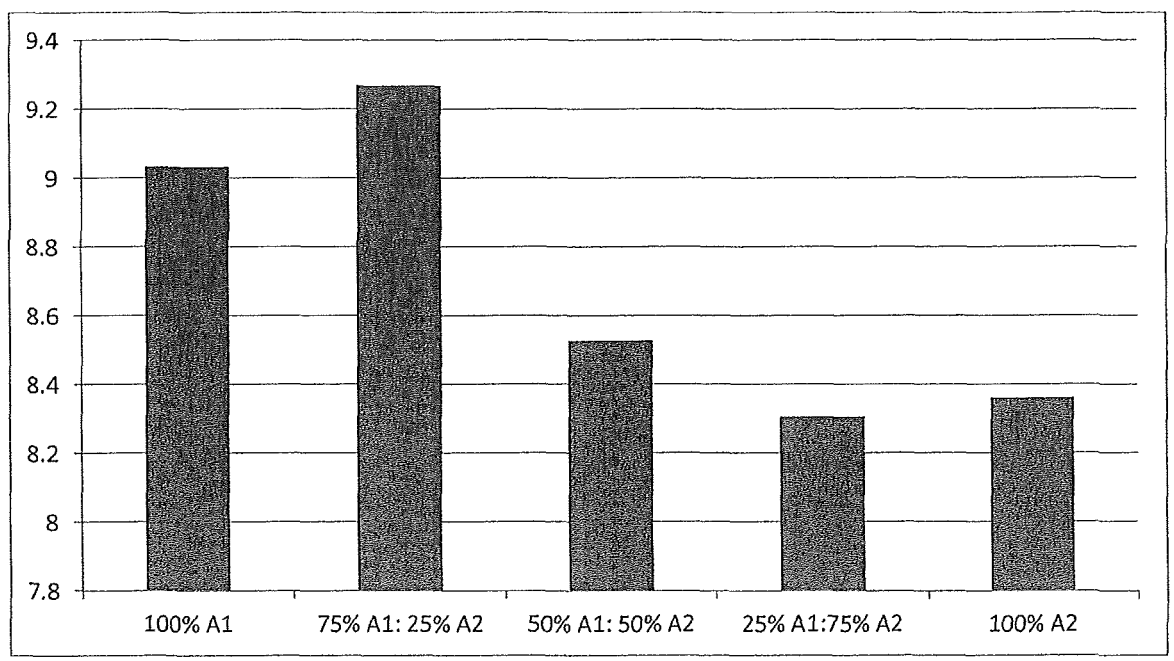
FIG. 3 shows jejunum DPPIV activity in rats fed varying ratios of beta-casein A1 and beta-casein A2.

The results of Example 2 show that a diet containing beta-casein A1 causes an increase in DPPIV acivity in the jejunum. The effect was not observed in the colon, presumably because glucose absorption occurs primarily in the small intestine, not the colon. Table 2 and FIG. 1 show that, relative to animals fed the A2 milk diet, animals fed the A1 milk diet demonstrated an increase in DPPIV activity in jejunum tissue, and this activity was persistent from acute through to chronic exposure to beta-casein A1 (or its peptide metabolites). The effect was not reversed, or otherwise affected, on administration of naxolone. Table 3 and FIG. 2 show no difference in DPPIV activity in colon tissue between animals fed the A1 milk diet and animals fed the A2 milk diet, whether under acute feeding or chronic feeding conditions. On investigating varying ratios of beta-casein A1 and beta-casein A2 in the diets, and as shown in Table 4 and FIG. 3, animals fed a diet containing beta-casein that is 100% beta-casein A1 showed a significant increase in jejunum DPPIV activity. This increase was also observed in animals fed the 75% A1:25% A2 diet. As the proportion of beta-casein A2 in the diet increases, i.e. 50% A1:50% A2 to 25% A1:75% A2 to 100% A2, the level of DPPIV activity decreased.

Example 2 therefore shows clearly that ingestion of beta-casein A2, instead of beta-casein A1, leads to lower levels of DPPIV activity in the jejunum, and consequently should lead to lower blood glucose levels.

Figure 4:
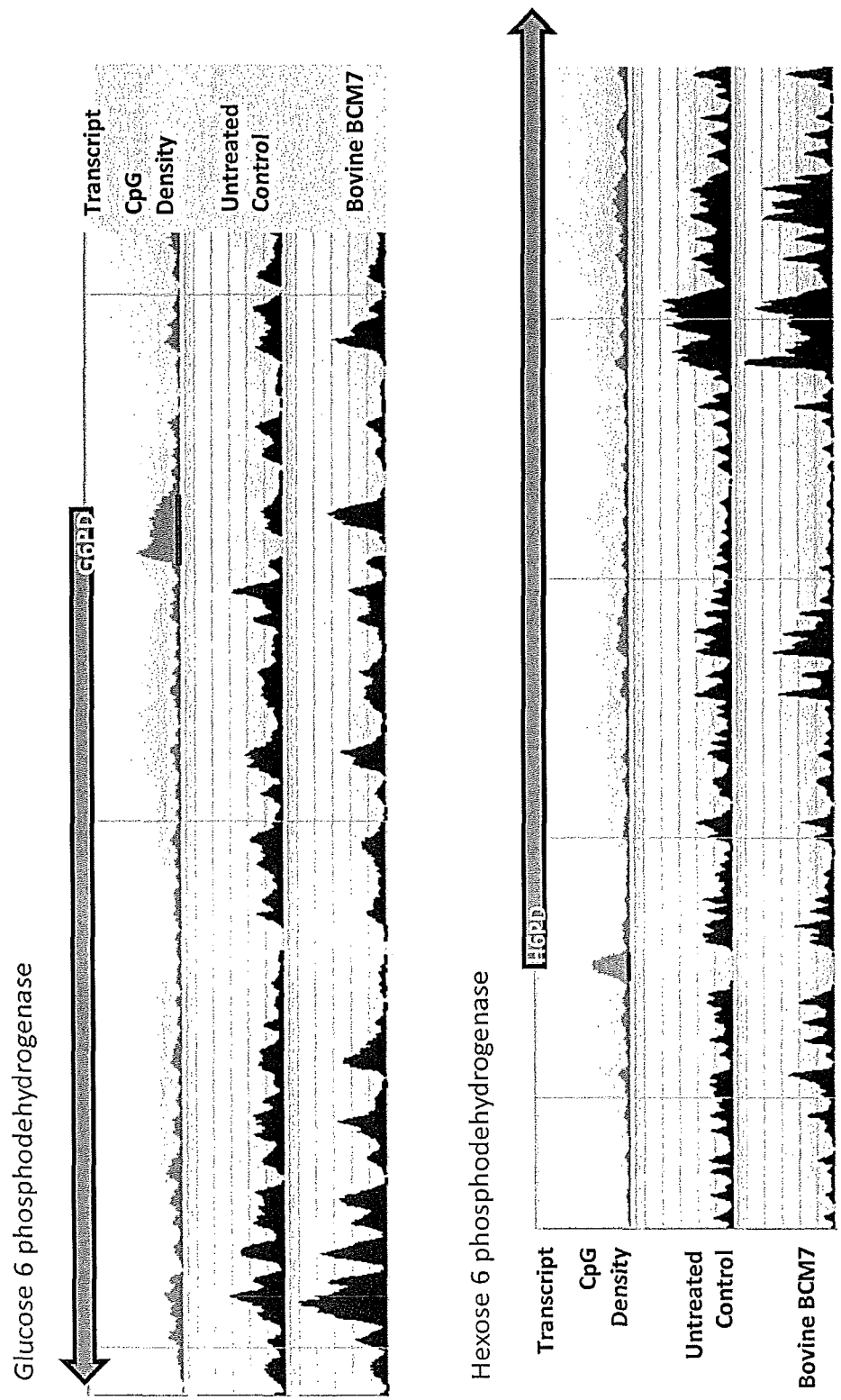
FIG. 4 shows DNA methylation changes in the genes corresponding to enzymes responsible for glucose metabolism and glucose homeostasis.

Example 3 shows DNA methylation changes in the genes responsible for glucose synthesis and glucose metabolism (FIG. 4) in human cells treated with BCM-7 for 4 hours. Further, this Example also shows the DNA methylation changes in the genes responsible for glucose homeostasis (Table 5). Lastly, Example 3 shows that the genes important for insulin signalling pathway and insulin sensitivity have an altered epigenetic status.

Figure 5:
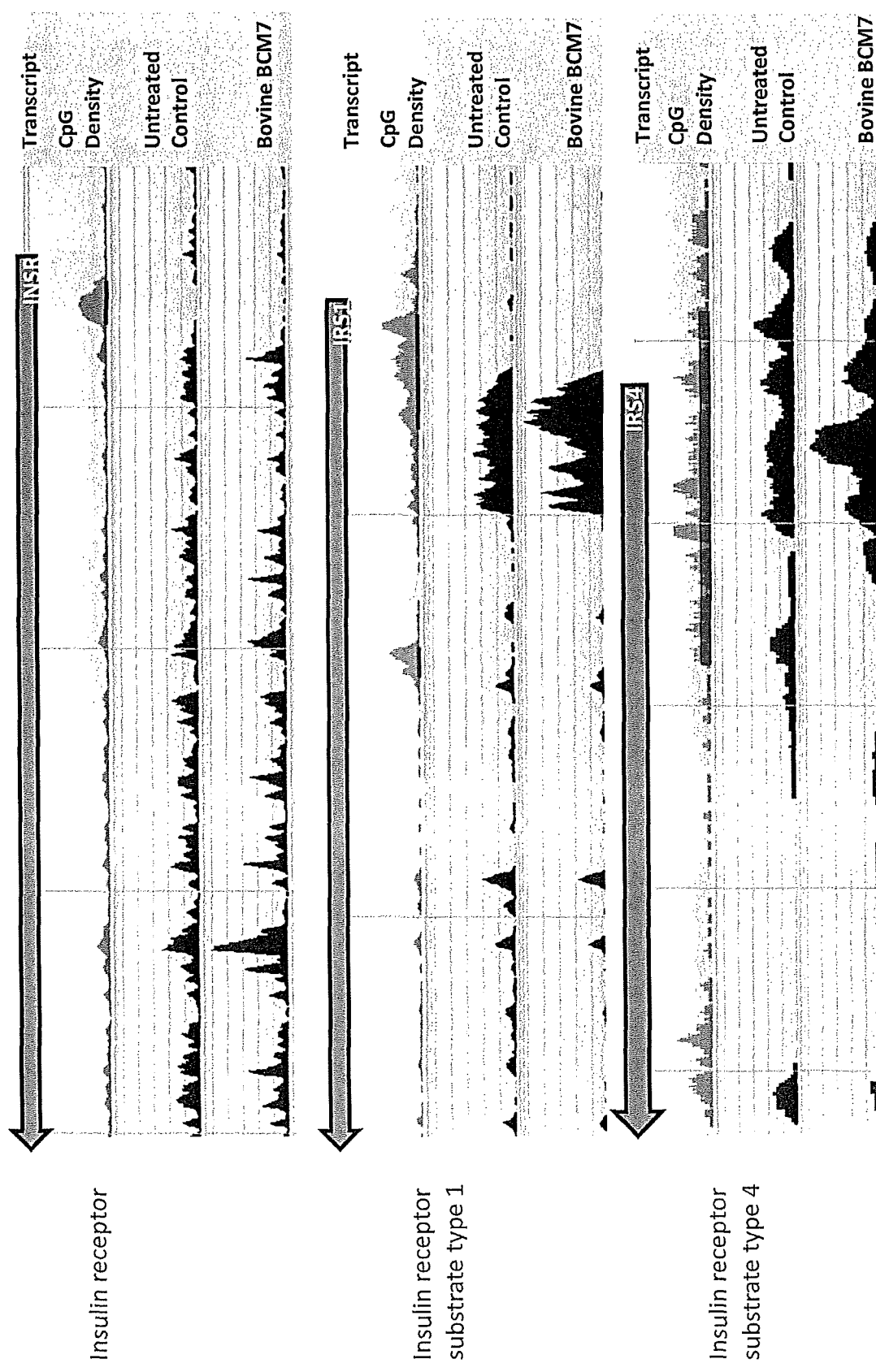
FIG. 5 shows DNA methylation changes in the genes corresponding to enzymes responsible for insulin receptor (INSR) and insulin receptor substrates (IRS1, ISR4).

The enzymes/proteins encoded by these genes mediate glucose sensitivity and glucose homeostasis under the influence of insulin and insulin receptor activation. As indicated in FIG. 5, the genes encoding insulin receptor (INSR) and insulin receptor substrates (IRS1, IRS4) are altered at the epigenetic level. This directly correlates to decreased insulin receptor formation and decreased insulin sensitivity as observed with type II diabetes mellitus.

Feedback regulation from glucose promotes insulin synthesis. However, due to down regulation of insulin receptor gene expression, there is decreased insulin sensitivity and disruption of glucose metabolism leading to altered glucose homeostasis. Since these changes are at the epigenetic level, they potentially have a life-long effect and in some cases may even be passed to next generations. Thus, beta-casein A1 (and BCM-7) effects insulin sensitivity at the cellular level due to an altered epigenetic status of the genes responsible for glucose homeostasis and insulin signalling.

Figure 6:
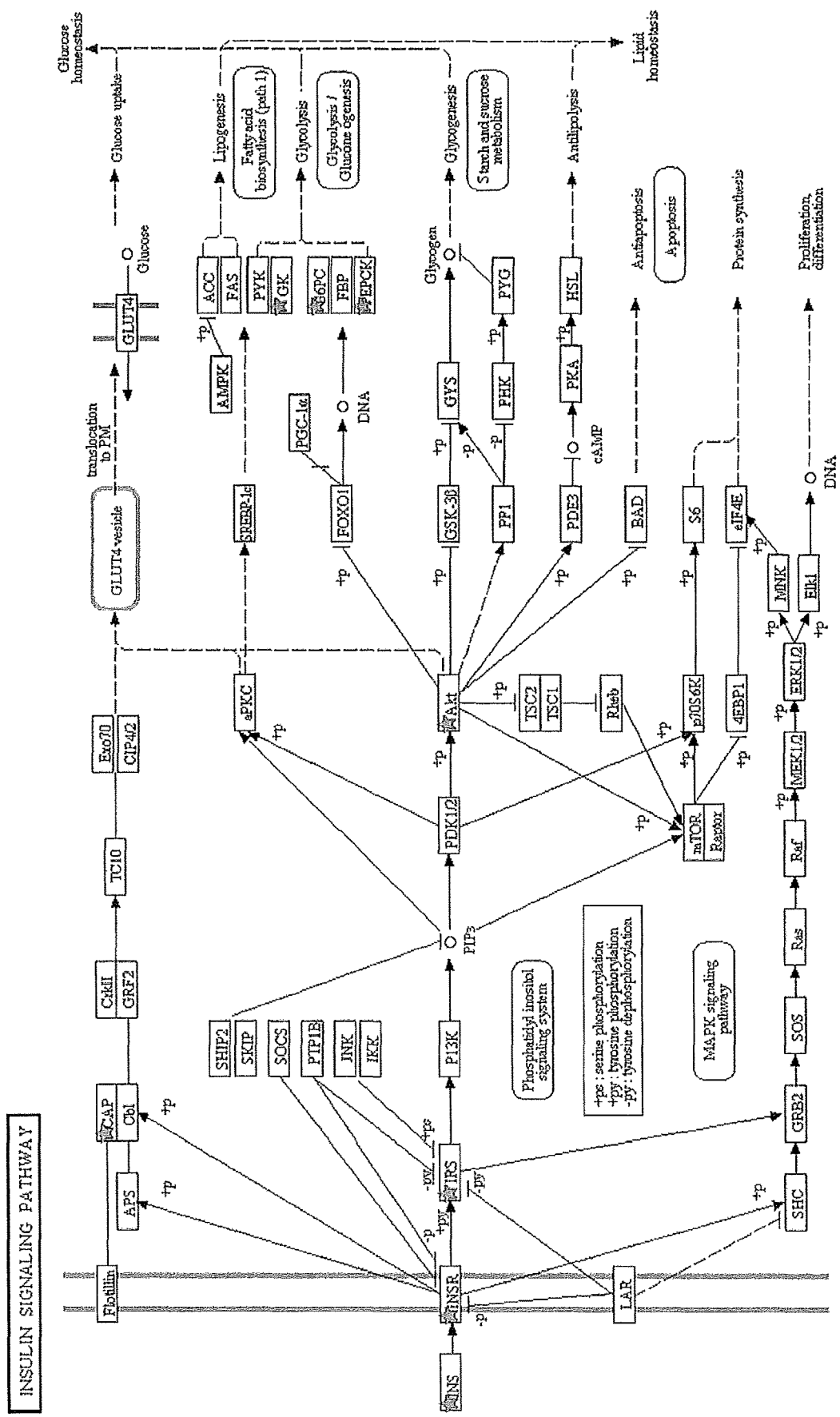
FIG. 6 shows the insulin pathway and the genes from this pathway which have an altered epigenetic status.

The transcripts and the functional ontology of each gene were analysed using the software application DAVID™ together with the Kyoto Encyclopaedia of Genes and Genomes (KEGG) to observe the interaction of the genes altered in the insulin signalling pathway. The genes which were epigenetically modified under the influence of BCM-7 after 4 hours are shown in FIG. 6 (indicated with a star). Although FIG. 6 is a summary representation and does not cover all the genes found to be epigenetically altered, it does demonstrate that BCM-7 affects insulin sensitivity at the receptor level through to the enzymes that metabolise glucose.

Figure 7:
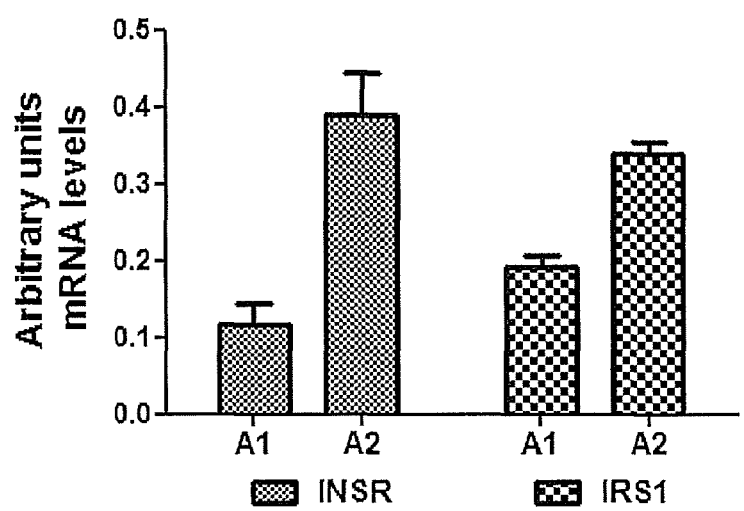
FIG. 7 shows the levels of mRNA for insulin receptor (INSR) and insulin receptor substrate (IRS1) expressed in the pancreas of NOD mice.

Example 4 indicates the changes in gene expression of key receptors involved in the insulin signalling pathway. Specifically, this Example focuses on the insulin receptor itself. NOD (non-obese diabetic) mice were fed an A1 diet or an A2 diet for 10 weeks followed by isolation of their pancreas. Quantification of mRNA levels of insulin receptor (INSR) and insulin receptor substrate type 1 (IRS1) was performed. As indicated in FIG. 7, mRNA levels of INSR and IRS1 were both lower in the pancreas from NOD mice (N=5) fed the A1 diet compared with NOD mice fed the A2 diet. This indicates that the A1 diet leads to decreased mRNA levels of insulin receptor. This coincides with the altered epigenetic status of INSR and IRS1 induced by BCM-7 in cells. Hence, beta-casein A1 decreases insulin sensitivity, which results in altered glucose metabolism and homeostasis.

These studies represent the first clear scientific evidence of a link between beta-casein A1 consumption and high levels of glucose in blood. Through the applicant's findings, an alternative potential solution is provided to the problems that are suffered by diabetics, i.e. the avoidance of beta-casein A1 in diet. The control of blood glucose levels requires daily, even hourly, vigilance by diabetics. Levels are manipulated by the injection of insulin and the strict regulation of food intake. Since the present invention leads generally to lower blood glucose levels, i.e. particularly by replacing foods containing beta-casein A1 with foods containing beta-casein A2, this represents a means for managing blood glucose homeostasis, decreasing insulin resistance and potentially reducing the frequency of insulin injections needed by diabetics and the amounts of insulin that need to be administered.

It is well-known that excessive amounts of carbohydrates, especially simple sugars, in the diet of humans increases the risk of developing insulin resistance which subsequently leads to downstream symptoms of conditions such as type II diabetes and metabolic syndrome. Since beta-casein A1 in the diet increases DPPIV activity and down regulates INSR and IRS1 and IRS4 gene expression relative to beta-casein A2, and therefore leads to high blood glucose levels, a diet that contains little or no beta-casein A1 is beneficial for health.

In practical terms, the benefits of the invention can be achieved for large populations by sourcing milk having a beta-casein content that is predominantly beta-casein A2 and producing products derived from that milk, and making that milk and those products available for the purpose of regulating blood glucose levels and management of the symptoms of diabetes and other conditions where hyperglycemia manifests.

The milk of cows can be tested for the relative proportions of beta-casein A1 and beta-casein A2. Alternatively, cows can be genetically tested for their ability to produce milk containing beta-casein A1 or beta-casein A2 or a combination of both. These techniques are well-known.

The present invention provides a solution that is comparatively easy to manage, i.e. avoidance of milk or milk products that contain beta-casein A1 and ensuring that milk and milk products in the diet contain beta-casein that is predominantly beta-casein A2, preferably 100% beta-casein A2.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to".

The invention is further described with reference to the following examples. It will be appreciated that the invention as claimed is not intended to be limited in any way by these examples.

EXAMPLES

Example 1

Feeding Methodology

Seventy two weaned (four week old) male Wistar rats were used. Following a 7-day acclimatisation period on a control diet, the rats were fed for either 12 or 60 hours with one of three diets: 100% A1 diet, 100% A2 diet, control diet (n=6 per treatment). The protein component of the diets were derived from skim milk (for the A1 and A2 diets) and on egg white (for the non-milk protein control diet), and were balanced for energy and macronutrient composition (see Table 1). Fifteen minutes before the end of the time period, rats received either naloxone or saline (control) via intra-peritoneal injection, and were then orally gavaged with a non-digestible tracer, titanium dioxide. Faecal and urine samples were collected at 7 time points over the following 24 hours, and stored at −20° C. (faecal) or −80° C. (urine) until they were analysed.

TABLE 1

Composition of diets

| | Product | | | | | |
| --- | --- | --- | --- | --- | --- | --- |
| | A1 milk diet | | A2 milk diet | | Control diet | |
| Ingredient | gm | kcal | gm | kcal | gm | kcal |
| Casein | 0 | 0 | 0 | 0 | 0 | 0 |
| A1 milk powder | 475 | 1691 | 0 | 0 | 0 | 0 |
| A2 milk powder | 0 | 0 | 468 | 1687 | 0 | 0 |
| DL-methionine | 3 | 12 | 3 | 12 | 0 | 0 |
| Egg whites (dried) | 0 | 0 | 0 | 0 | 200 | 800 |
| Corn starch | 150 | 600 | 150 | 600 | 153 | 612 |
| Sucrose | 288 | 1152 | 294 | 1176 | 500 | 2000 |
| Cellulose, BW200 | 50 | 0 | 50 | 0 | 50 | 0 |
| Corn oil | 45.2 | 406.8 | 43 | 387 | 50 | 450 |
| Mineral mix S10001 | 35 | 0 | 35 | 0 | 35 | 0 |
| Biotin, 1% | 0 | 0 | 0 | 0 | 0.4 | 0 |
| Vitamin mix V10001 | 10 | 40 | 10 | 40 | 10 | 40 |
| Choline bitartrate | 2 | 0 | 2 | 0 | 2 | 0 |
| Total | 1058.2 | 3902 | 1055 | 3902 | 1000.4 | 3902 |

Example 2

DPPIV Activity

Tissue from the jejunum and colon of rats fed according to Example 1 was quantified for dipeptidyl peptidase IV (DPPIV) activity using a commercial kit (Kit BML-AK498, ENZO Life Sciences, USA). Tissue samples (50 mg) were homogenised in Tris (100 mM, pH 8) and quantified by the addition of Gly-Pro-4-Nitroanilide (Sigma)>Dipeptidyl Peptidase>Gly-Pro+p-Nitroaniline incubated in Tris (100 mM, pH 8) for 15 minutes at 37° C. The reaction was stopped with acetate buffer (1M, pH 4.2) and the absorbance read in a plate reader at 405 nm and compared to a reference standard curve (Sigma) to calculate activity. One unit produces 1.0 mM of 4-Nitroaniline from Gly-Pro-4-nitroaniline per minute in 0.1 M Tris/HCl at pH 8.0 at 37° C. The results, shown in Tables 2 to 4 and in FIGS. 1 to 3, clearly indicate that beta-casein A1 increases DPPIV activity in the jejunum. DPPIV activity is expressed in units of nmol/min/µg protein. Note that the rats used for the study of varying ratios of beta-casein A1 and beta-casein A2 (Table 4) were conditioned differently (purified rat diet AIN-76A).

TABLE 2

Jejunum DPPIV activity

| | | A1 | Std Dev | A2 | Std Dev |
| --- | --- | --- | --- | --- | --- |
| Saline | 12 | 39.19 | 9.05 | 29.94 | 4.66 |
| Naloxone | 12 | 35.43 | 6.68 | 30.38 | 10.25 |
| Saline | 60 | 37.35 | 7.92 | 26.15 | 3.58 |
| Naloxone | 60 | 39.39 | 6.43 | 36.56 | 14.18 |

TABLE 3

Colon DPPIV activity

|  | A1 | Std Dev | A2 | Std Dev |
|---|---|---|---|---|
| Saline | 12 | 6.53 | 1.18 | 6.79 | 0.74 |
| Naloxone | 12 | 6.52 | 1.33 | 6.68 | 0.70 |
| Saline | 60 | 6.94 | 0.81 | 7.19 | 0.63 |
| Naloxone | 60 | 7.03 | 1.33 | 6.87 | 0.64 |

TABLE 4

Jejunum DPPIV activity for varying A1:A2 ratios

|  | Jejunum DPPIV activity | Std Dev |
|---|---|---|
| 100% A1 | 9.03 | 1.89 |
| 75% A1:25% A2 | 9.27 | 1.68 |
| 50% A1:50% A2 | 8.53 | 2.26 |
| 25% A1:75% A2 | 8.31 | 1.32 |
| 100% A2 | 8.36 | 1.18 |

Example 3

Effect of BCM-7 on DNA Methylation Levels

Shifts in global DNA methylation patterns induced by BCM-7 were investigated using methyl-CpG binding domain (MBD) protein-enriched genome sequencing (MBD-seq) as described previously (Trivedi M., et al., *Mol. Pharm.* 2014), whereas mRNA translation microarray data was obtained using an Agilent V3 microarray chip, from non-treated control SH-SY5Y cells and cells treated for 4 hours with 1 μM BCM-7.

Genomic DNA was extracted from samples using the Easy DNA kit (Invitrogen K1800-01) using the appropriate protocol for cell lines. Fragmentation was performed on a Covaris S2 ultrasonicator using the following settings: duty cycle 10%, intensity 5, 200 cycles per burst during 200 sec. Fragments were obtained having an average length of 200 bp. The power mode is frequency sweeping, temperature 6-8° C., water level 12. A maximum of 5 μg was loaded in 130 μl Tris-EDTA in a microtube with AFA intensifier. For samples with less DNA input (down to 500 ng) the DNA was diluted 1:5 in TrisEDTA. DNA with an input from 5-3 μg was analysed on the Agilent 2100 using a DNA 1000 chip. DNA with an input lower than 3 μg was concentrated in a rotary evaporator to 25 μl and the fragment distribution was checked on a high sensitivity DNA chip. Methylated DNA was captured using the MethylCap kit (Diagenode, Belgium). The yield was typically between 0.5 and 8 ng of total captured DNA. Fragments were subsequently sequenced using an Illumina Genome Analyzer II. The concentrations of fragmented and captured DNA were determined on a Fluostar Optima plate reader with the Quant-iT PicoGreen dsDNA Assay Kit (Invitrogen P7589) at 480/520 nm.

To prepare the DNA library, a DNA Sample Prep Master Mix Set 1 (NEB E6040) was used in combination with a Multiplexing Sample Preparation Oligo Kit (96 samples, Illumina PE-400-1001). The entire fragmented DNA was utilised and followed the NEB protocols, using the multiplexing sequencing adapters provided in the Multiplexing Sample Preparation Oligo Kit. Size selection of the library was carried out on a 2% agarose gel (Low Range Ultra Agarose Biorad 161-3107). A 1 Kb Plus ladder (Invitrogen 10787-018) was used and a gel was run at 120 V for 2 hrs. A fragment of 300 bps+/− 50 bps was excised and eluted on a Qiagen Gel Extraction Kit column (Qiagen 28704) and eluted in 23 μl EB.

The Illumina library amplification index protocol was used with the following alterations: 22 μl DNA was used and performed 21 cycles run. The sample was purified on a Qiaquick PCR Purification column (Qiagen 28101) and eluted in 50 μl EB, 1:5 diluted, and concentrated in a rotary evaporator to 10 μl. 1 μl was applied to an Agilent 2100 HS DNA chip and the concentration was determined by smear analysis on the Agilent 2100. The samples were diluted to 10 nM. After denaturation with NaOH the samples were diluted to 16 pM. The Paired-End flow cell was prepared according to the Cluster Station User Guide. Sequencing was performed according to the HiSeq user guide (performing a Multiplexed PE Run), with 2×51 cycles for the paired end runs.

TABLE 5

Genes Regulated by BCM-7 treatment involved in glucose homeostasis ($P < 0.01$, $FDR < 0.1$)

Genes

| | | | |
|---|---|---|---|
| CREM | AKR1A1 | AKT1 | SLC2A9 |
| SORBS1 | PGM1 | SORD | EDNRA |
| CACNA1E | PCK1 | SSTR5 | ADRA1B |
| TCF7L2 | SLC5A1 | RPH3AL | EDN1 |
| INS | GCKR | PLSCR3 | ALDH5A1 |
| IGF2 | ALMS1 | STAT3 | PPARD |
| CPT1A | HK2 | G6PC | CYB5R4 |
| PGM2L1 | PDK1 | PDK2 | FOXO3 |
| SLC37A4 | IRS1 | STXBP4 | GCK |
| CACNA1C | CAV3 | YES1 | MLXIPL |
| SLC2A3 | PPARG | INSR | SERPINE1 |
| PFKM | KLF15 | CACNA1A | SLC30A8 |
| PTPN11 | ADIPOQ | GAPDHS | PGM5 |
| HNF1A | WFS1 | SLC2A5 | PTCH1 |
| WDTC1 | PDK3 | H6PD | DBH |

Whole genome DNA MBD-seq revealed differentially methylated transcripts (DMTs), as defined by false discovery rate (FDR)<0.1 and ANOVA followed by post-hoc student's t-test ($p<0.05$). Transcripts included both genes and non-coding RNAs that were differentially methylated/transcribed. The epigenetic changes as well as the transcription changes induced by BCM-7 in specific biological or functionally relevant pathways were evaluated using the Ingenuity Pathway Analysis (IPA) tool and pathways exhibiting the highest impact were identified. The results are shown in Table 5. The changes in the epigenetic status of genes responsible for the glucose metabolism, synthesis and glucose homeostasis are also reported to be altered under BCM-7, as shown in FIGS. 5 and 6.

Example 4

Effect of Beta-Caseins on Insulin Receptor

NOD mice (male and female) were fed a diet enriched in either A1 or A2 beta-casein milk protein from weaning. These diets were made by Specialty Feeds Australia to ensure adequate composition and nutrition. Cohorts of mice (n=10) from each gender and diet were euthanased at 10 W, 20 W and at the time of dissection various samples were collected and stored at −80° C. 40 NOD mice were followed in this study: 10 per group (male/female; A1/A2); 10 were euthanased at 10 W and 20 W. Pancreas were collected and frozen in RNAlater™.

RNA from tissues for the analysis of RNA transcription was isolated using an RNAqueous®-4PCR kit from Ambion (Austin, Tex.). The procedure followed was according to the manufacturer's protocol. The isolated RNA was treated with DNase to purify the RNA followed by RNA quantification using a ND-1000 NanoDrop spectrophotometer. Further, cDNA was synthesised as described previously using the first-strand cDNA synthesis from Roche (Indianapolis, Ind.). 1 mg of RNA, 1 mM dNTP mix, 60 mM random hexamer primers, with sufficient molecular biology grade H20 was added to achieve a final sample volume of 13 ml. Next, the samples were denatured at 65° C. for 5 minutes and then placed on ice. Transcriptor RT (20 units/ml) (Roche), Protector RNase inhibitor (40 U/ml) (Roche), 5 Transcriptor Reverse Transcriptase Reaction Buffer (Roche), and molecular biology grade H20 were added to a final volume of 7 ml in the second part of the reaction and the final volume was adjusted to 20 ml. This was followed by incubation in the PTCThermocycler (MJ Research, St. Bruno, QC, Canada) at 25° C. for 10 minutes and ended by 30 minutes at 55° C. Lastly, the reverse-transcriptase enzyme was inhibited by incubation at 85° C. for 5 minutes.

TABLE 6

Primer sequences for qRTPCR

| Sr No | Gene | Forward 5'→3' | Reverse 5'→3' |
|---|---|---|---|
| | | (SEQ ID NO: 1) | (SEQ ID NO: 2) |
| 1 | INSR | ATCCAGCCTGGGTGACATAG | AGGGAGTTTGGACAACAACG |
| | | (SEQ ID NO: 3) | (SEQ ID NO: 4) |
| 2 | IRS1 | AAATTAGCCTGCCCTTCGTT | TGCTGGAAACTTCTGCATTG |

Subsequently, the qRT-PCR assay was performed on triplicate samples using the LightCycler 480 qRT-PCR machine from Roche (Trivedi et al., Mol. Pharmcol. 2014). qRT-PCR was performed using 5 ml of cDNA template, 10 mM sense and antisense primers, 10 ml SYBR Green I Master from Roche, as well as dH20 in a final volume of 20 ml. The list of primers used for this purpose are shown in Table 6. The samples were put through the following protocol; incubation for 5 minutes at 95° C., and then 45 cycles of 95° C. for 10 seconds, 60° C. for 20 seconds, and 72° C. for 30 seconds, followed by a single cycle of 95° C. for 5 seconds, 1 minute at 65° C., and 97° C. for the melting curve, followed by cooling at 40° C. for 90 seconds. No template controls (NTC) were run on the plate, and the dissociation curves were generated to determine the non-specific products and this was normalized to avoid any non-specific amplification. Data were analysed using the Roche quantification method and were normalised to beta-actin levels.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. A method for treating hyperglycemia in a non-diabetic animal, where the method comprises a non-diabetic animal in need thereof consuming a composition containing beta-casein or providing the composition to the animal for consumption, wherein the beta-casein comprises at least 75% by weight beta-casein A2.

2. The method as claimed in claim 1, wherein the beta-casein comprises at least 90% by weight beta-casein A2.

3. The method as claimed in claim 1, wherein the beta-casein comprises 100% beta-casein A2.

4. The method as claimed in claim 1, wherein the composition is milk or a milk product.

5. The method as claimed in claim 4, wherein the milk is fresh milk, milk powder, liquid milk reconstituted from powder, skim milk, homogenised milk, condensed milk, evaporated milk, pasteurised milk, or non-pasteurised milk.

6. The method as claimed in claim 4, wherein the milk product is cream, yoghurt, quark, cheese, butter, or ice cream.

7. The method as claimed in claim 1, wherein the animal is a human, dog, or cat.

8. The method as claimed in claim 1, wherein the beta-casein comprises 95% beta-casein A2.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: ISNR -Forward Sequence

<400> SEQUENCE: 1
atccagcctg ggtgacatag                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: INSR -Reverse Sequence

<400> SEQUENCE: 2
agggagtttg gacaacaacg                                              20

<210> SEQ ID NO 3
<211> LENGTH: 20
<212> TYPE: DNA
<213> ORGANISM: Artificial Sequence
```

```
<220> FEATURE:
<223> OTHER INFORMATION: Synthetic Polynucleotide
<220> FEATURE:
<221> NAME/KEY: misc_feature
<223> OTHER INFORMATION: IRS1 -Forward Sequence

<400> SEQUENCE: 3
aaattagcct gcccttcgtt                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: IRS1- Reverse Sequence

<400> SEQUENCE: 4
tgctggaaac ttctgcattg                                               20
```